US010286037B2

(12) United States Patent
Kranz et al.

(10) Patent No.: US 10,286,037 B2
(45) Date of Patent: May 14, 2019

(54) METHODS OF PRODUCING LYOPHILIZED POLYPEPTIDE COMPOSITION FORMULATIONS COMPRISING VOLATILE ADDITIVES

(75) Inventors: James Kranz, King of Prussia, PA (US); Joseph Rinella, King of Prussia, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 883 days.

(21) Appl. No.: 13/984,536

(22) PCT Filed: Feb. 9, 2012

(86) PCT No.: PCT/US2012/024452
§ 371 (c)(1),
(2), (4) Date: Aug. 9, 2013

(87) PCT Pub. No.: WO2012/109429
PCT Pub. Date: Aug. 16, 2012

(65) Prior Publication Data
US 2014/0044717 A1    Feb. 13, 2014

Related U.S. Application Data

(60) Provisional application No. 61/440,918, filed on Feb. 9, 2011.

(51) Int. Cl.
*A61K 39/395* (2006.01)
*A61K 38/16* (2006.01)
*C07K 16/22* (2006.01)
*C07K 16/24* (2006.01)
*C07K 16/28* (2006.01)
*A61K 38/26* (2006.01)

(52) U.S. Cl.
CPC .............. *A61K 38/16* (2013.01); *A61K 38/26* (2013.01); *A61K 39/39591* (2013.01); *C07K 16/22* (2013.01); *C07K 16/244* (2013.01); *C07K 16/2878* (2013.01); *C07K 16/2887* (2013.01); *C07K 2317/569* (2013.01)

(58) Field of Classification Search
None
See application file for complete search history.

(56) References Cited

U.S. PATENT DOCUMENTS

| 7,141,547 B2* | 11/2006 | Rosen | A61K 38/04 514/11.7 |
|---|---|---|---|
| 2003/0017169 A1 | 1/2003 | Pestka et al. | |
| 2007/0190163 A1 | 8/2007 | Malaknov et al. | |
| 2010/0158814 A1 | 6/2010 | Bussat et al. | |

FOREIGN PATENT DOCUMENTS

| WO | WO 99/42125 | 8/1999 |
|---|---|---|
| WO | WO9942125 A1 | 8/1999 |
| WO | WO 2006/055532 A2 | 5/2006 |
| WO | WO2006055532 A2 | 5/2006 |
| WO | WO 2007/056681 A2 | 5/2007 |
| WO | WO2007056681 A2 | 5/2007 |
| WO | WO2008071679 A1 | 6/2008 |
| WO | WO2008073458 A2 | 6/2008 |
| WO | WO 2009/066956 | 5/2009 |
| WO | WO 2011/017070 A1 | 2/2011 |
| WO | WO 2011/017330 A1 | 2/2011 |

OTHER PUBLICATIONS

Wittaya-Areekul et al, Journal of pharmaceutical sciences, 1998, vol. 87, No. 4, p. 491-495.*
Teagarden, D.L., et al., European Journal of Pharmaceutical Sciences, 2002, vol. 15, pp. 115-133.
Schwegman, J.J., et al., Pharmaceutical Development and Technology, 2005, vol. 10, pp. 151-173.
Yong, et al., *International Journal of Pharmaceutics*, Conformational and Bioactivity Analysis of Insulin: Freeze-drying TBA/water co-solvent system in the presence of surfactant and sugar, 371:71-81 (2008).
Bush et al., Safety, tolerability, pharmacodynamics, and pharmacokinetics of albiglutide, a long-acting glucagon-like peptide-1 mimetic, in healthy subjects, *Diabetes, Obesity and Metabolism*, 11:498 (2009).
Yao et al., The design and application of drug lyophilization technology, *China Medical Science Press*, 122-123 (2007).
Zhang Yong et al., Conformational and bioactivity analysis of insulin: Freeze-drying TBA/water co-solvent system in the presence of surfactant and sugar, *International Journal of Pharmaceutics*, 371:71-81 (2009).

* cited by examiner

*Primary Examiner* — Yunsoo Kim
(74) *Attorney, Agent, or Firm* — Leah M. Octavio; Fang Qian

(57) ABSTRACT

The invention is directed to a method for producing a polypeptide composition comprising: combining a polypeptide with a volatile additive to form a liquid mixture and lyophilizing the liquid mixture to obtain a lyophilized polypeptide composition.

16 Claims, 12 Drawing Sheets
Specification includes a Sequence Listing.

Figure 5

SEQ ID NO.: 1

```
HGEGTFTSDVSSYLEGQAAKEFIAWLVKGRHGEGTFTSDVSSYLEGQAAKEFIAWLVKGR  60
DAHKSEVAHRFKDLGEENFKALVLIAFAQYLQQCPFEDHVKLVNEVTEFAKTCVADESAE 120
NCDKSLHTL FGDKLCTVATLRETYGEMADCCAKQEPERNECFLQHKDDNPNLPRLVRPE 180
VDVMCTAFHDNEETFLKKYLYEIARRHPYFYAPELLFFAKRYKAAFTECCQAADKAACLL 240
PKLDELRDEGKASSAKQRLKCASLQKFGERAFKAWAVARLSQRFPKAEFAEVSKLVTDLT 300
KVHTECCHGDLLECADDRADLAKYICENQDSISSKLKECCEKPLLEKSHCIAEVENDEMP 360
ADLPSLAADFVESKDVCKNYAEAKDVFLGMFLYEYARRHPDYSVVLLLRLAKTYETTLEK 420
CCAAADPHECYAKVFDEFKPLVEEPQNLIKQNCELFEQLGEYKFQNALLVRYTKKVPQVS 480
TPTLVEVSRNLGKVGSKCCKHPEAKRMPCAEDYLSVVLNQLCVLHEKTPVSDRVTKCCTE 540
SLVNRRPCFSALEVDETYVPKEFNAETFTFHADICTLSEKERQIKKQTALVELVKHKPKA 600
TKEQLKAVMDDFAAFVEKCCKADDKETCFAEEGKKLVAASQAALGL               674
```

Figure 8

SEQ ID NO: 3  anti-NOGO mAb Heavy chain

MGWSCIILFL VATATGVHSQ VQLVQSGAEV KKPGASVKVS CKASGYTFTS YWMHWVRQAP
GQGLEWIGNI NPSNGGTNYN EKFKSKATMT RDTSTSTAYM ELSSLRSEDT AVYYCELMQG
YWGQGTLVTV SSASTKGPSV FPLAPSSKST SGGTAALGCL VKDYFPEPVT VSWNSGALTS
GVHTFPAVLQ SSGLYSLSSV VTVPSSSLGT QTYICNVNHK PSNTKVDKKV EPKSCDKTHT
CPPCPAPELA GAPSVFLFPP KPKDTLMISR TPEVTCVVVD VSHEDPEVKF NWYVDGVEVH
NAKTKPREEQ YNSTYRVVSV LTVLHQDWLN GKEYKCKVSN KALPAPIEKT ISKAKGQPRE
PQVYTLPPSR DELTKNQVSL TCLVKGFYPS DIAVEWESNG QPENNYKTTP PVLDSDGSFF
LYSKLTVDKS RWQQGNVFSC SVMHEALHNH YTQKSLSLSP GK

SEQ ID NO: 4  anti-NOGO mAb light chain

MGWSCIILFL VATATGVHSD IVMTQSPLSN PVTLGQPVSI SCRSSKSLLY KDGKTYLNWF
LQRPGQSPQL LIYLMSTRAS GVPDRFSGGG SGTDFTLKIS RVEAEDVGVY YCQQLVEYPL
TFGQGTKLEI KRTVAAPSVF IFPPSDEQLK SGTASVVCLL NNFYPREAKV QWKVDNALQS
GNSQESVTEQ DSKDSTYSLS STLTLSKADY EKHKVYACEV THQGLSSPVT KSFNRGEC

Figure 9

```
SEQ ID NO: 5   anti-TNFR1 dAb

EVQLLESGGG LVQPGGSLRL SCAASGFTFA HETMVWVRQA PGKGLEWVSH IPPDGQDPFY
ADSVKGRFTI SRDNSKNTLY LQMNSLRAED TAVYHCALLP KRGPWFDYWG QGTLVTVSS
```

Figure 10

```
SEQ ID NO: 6  IL18

YFGKLESKLS VIRNLNDQVL FIDQGNRPLF EDMTDSDCRD NAPRTIFIIS

MYKDSQPRGM AVTISVKCEK ISTLSCENKI ISFKEMNPPD NIKDTKSDII

FFQRSVPGHD NKMQFESSSY EGYFLACEKE RDLFKLILKK EDELGDRSIM

FTVQNED
```

Figure 11

SEQ ID NO: 7  anti-IL5 mAb Heavy chain

QVTLRESGPA LVKPTQTLTL TCTVSGFSLT SYSVHWVRQP PGKGLEWLGV

IWASGGTDYN SALMSRLSIS KDTSRNQVVL TMTNMDPVDT ATYYCARDPP

SSLLRLDYWG RGTPVTVSSA STKGPSVFPL APSSKSTSGG TAALGCLVKD

YFPEPVTVSW NSGALTSGVH TFPAVLQSSG LYSLSSVVTV PSSSLGTQTY

ICNVNHKPSN TKVDKRVEPK SCDKTHTCPP CPAPELLGGP SVFLFPPKPK

DTLMISRTPE VTCVVVDVSH EDPEVKFNWY VDGVEVHNAK TKPREEQYNS

TYRVVSVLTV LHQDWLNGKE YKCKVSNKAL PAPIEKTISK AKGQPREPQV

YTLPPSREEM TKNQVSLTCL VKGFYPSDIA VEWESNGQPE NNYKTTPPVL

DSDGSFFLYS KLTVDKSRWQ QGNVFSCSVM HEALHNHYTQ KSLSLSPGK

SEQ ID NO: 8  anti-IL5 mAb light chain

DIVMTQSPDS LAVSLGERAT INCKSSQSLL NSGNQKNYLA WYQQKPGQPP

KLLIYGASTR ESGVPDRFSG SGSGTDFTLT ISSLQAEDVA VYYCQNVHSF

PFTFGGGTKL EIKRTVAAPS VFIFPPSDEQ LKSGTASVVC LLNNFYPREA

KVQWKVDNAL QSGNSQESVT EQDSKDSTYS LSSTLTLSKA DYEKHKVYAC

EVTHQGLSSP VTKSFNRGEC

Figure 12

```
SEQ ID NO: 9  anti-CD20 VH

MFLGLSWIFL LAILKGVQCE VQLVESGGGL VPQGRSLRLS CAASGFTFND

YAMHWVRQAP GKGLEWVSTI SWNSGSIGYA DSVKGRFTIS RDNAKKSLYL

QMNSLRAEDT ALYYCAKDIQ YGNYYYGMDV WGQGTTVTVS S

SEQ ID NO: 10  anti-CD20 VL

MEAPAQLLFL LLLWLPDTTG EIVLTQSPAT LSLSPGERAT LSCRASQSVS

SYLAWYQQKP GQAPRLLIYD ASNRATGIPA RFSGSGSGTD FTLTISSLEP

EDFAVYYCQQ RSNWPITFGQ GTRLEIK
```

METHODS OF PRODUCING LYOPHILIZED POLYPEPTIDE COMPOSITION FORMULATIONS COMPRISING VOLATILE ADDITIVES

This application is a 371 of International Application No. PCT/US2012/024452, filed Feb. 9, 2012, which claims the benefit of 61/440,918, filed Feb. 9, 2011, both of which are herein incorporated by reference.

FIELD OF THE INVENTION

The present invention relates to formulations useful for reducing the reconstitution time of lyophilized biological molecules and methods of use.

BACKGROUND OF THE INVENTION

Lyophilization is a process which removes solvent from a solution to form solid or powder which is stable and easier to store at elevated temperature than the liquid. Lyophilization, also known as freeze drying, involves freezing followed by sublimation. The resulting lyophilized matter may be stored without refrigeration, reducing storage and transportation costs of the substance as well as the storage space required for the product. It also can reduce the weight of the product, which similarly reduces shipping and related costs. Lyophilization is particularly useful for preserving and storing various biological molecules, because it increases their shelf-life.

Biological molecules are more difficult to stabilize via formulation than small molecules due to the number of chemical groups and dependence of stability on maintaining native folding. For this reason, many commercial biological molecules are lyophilized. In general, lyophilization improves stability through (i) the removal of water (since most biologic chemical degradations are hydrolytic) and (ii) decreasing the overall mobility of the system (since dynamic movement of side chains and molecules is necessary for chemical and physical degradation events to occur).

Lyophilized biological molecules are reconstituted prior to use, often in the very containers in which they were lyophilized and stored. Short reconstitution time is preferable for both physicians and patients. If the reconstitution time of the lyophilized biological molecule is too long, it will increase the preparation time thus making it difficult to administrate to many patients at the same. In addition, many biological molecules are designed to be administered by the patients themselves. A shorter reconstitution time ensures that patients will completely reconstitute the biological molecule before administration, thus improving safety and efficacy.

Previous efforts to reduce reconstitution time have focused primarily on the formulation of the reconstitution buffer. In contrast, the present invention is directed to the addition of a volatile additive to the formulation of the buffer used for lyophilization of a biological molecule. Thus, there is a need for methods and compositions for reducing the reconstitution time of a lyophilized biological molecule.

SUMMARY OF THE INVENTION

The present invention is directed to a method for producing a polypeptide composition comprising: combining a polypeptide with a volatile additive to form a liquid mixture and lyophilizing the liquid mixture to obtain a lyophilized polypeptide composition.

The present invention is also directed to a method for reducing the reconstitution time of a lyophilized polypeptide composition comprising: a) lyophilizing a liquid mixture comprising the polypeptide, wherein the liquid mixture comprises a volatile additive and b) reconstituting the lyophilized polypeptide with a sufficient amount of a pharmaceutically acceptable dispersing agent to the lyophilized polypeptide composition to yield a liquid polypeptide composition, wherein time for reconstituting the polypeptide lyophilized in the presence of the volatile additive is less than the time for reconstituting the same polypeptide lyophilized in the absence of the volatile additive.

The present invention is also directed to a method for producing a liquid polypeptide composition comprising: obtaining a lyophilized polypeptide produced by a method of the present invention, and reconstituting the lyophilized polypeptide with a sufficient amount of a pharmaceutically acceptable dispersing agent to yield a liquid polypeptide composition.

The present invention is also directed to a formulation suitable for lyophilization of a polypeptide.

The present invention is also directed to a dry polypeptide composition produced by a method of the present invention.

The present invention is also directed to a liquid polypeptide composition produced by a method of the present invention.

BRIEF DESCRIPTION OF THE DRAWINGS

FIG. 5. Amino acid sequence of Albiglutide (SEQ ID NO:1).

FIG. 8. Amino acid sequence of anti-NOGO mAb heavy (SEQ ID NO: 3) and light chains (SEQ ID NO: 4).

FIG. 9. Amino acid sequence of anti-TNFR1 dAb (SEQ ID NO: 5).

FIG. 10. Amino acid sequence of IL18 (SEQ ID NO: 6).

FIG. 11. Amino acid sequence of anti-IL5 heavy (SEQ ID NO: 7) and light chains (SEQ ID NO: 8).

FIG. 12. Amino acid sequence of anti-CD20 VH (SEQ ID NO: 9) and VL domains (SEQ ID NO: 10).

DETAILED DESCRIPTION OF THE INVENTION

Figure 1:
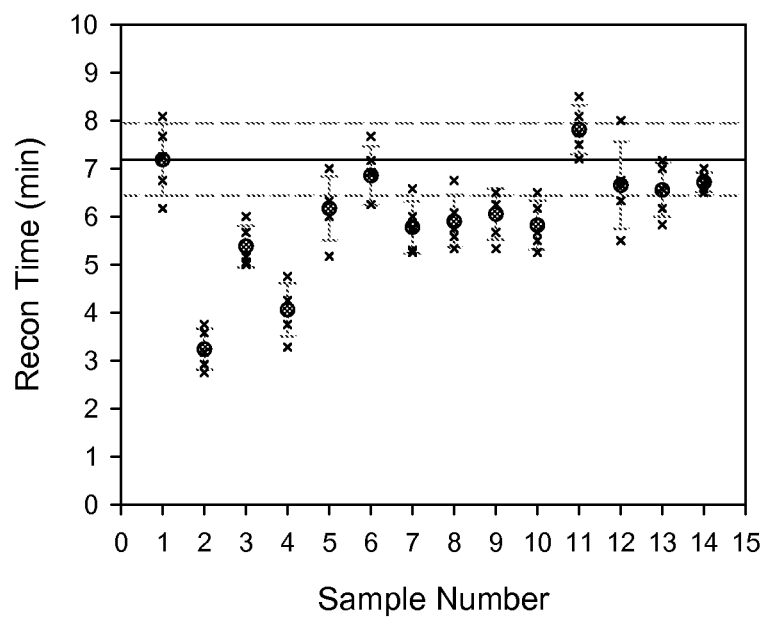
FIG. 1. Plots of lyophile reconstitution times using shaking method.

The present invention provides, inter alia, lyophilization formulations. The invention also provides, inter alia, methods of making and methods of using lyophilization formulations. It has been discovered by the inventors that when a volatile additive is added to a lyophilization formulation for a polypeptide reconstitution times for the lyophilized polypeptide are reduced. The present invention is also directed to a dry polypeptide composition produced by a method of the present invention.

The invention provides a number of methods, reagents, and compounds that can be used for producing a polypeptide composition comprising: combining a polypeptide with a volatile additive to form a liquid mixture and lyophilizing the liquid mixture to obtain a lyophilized polypeptide composition.

Methods for lyophilizing polypeptides from liquid solutions, and products comprising lyophilized polypeptides obtained from such lyophilized liquid solutions, are provided herein. In certain embodiments, the volatile additive is dissolved in aqueous solution containing the polypeptide and lyophilized to provide solid compositions containing the lyophilized polypeptide. In certain embodiments, these solid compositions containing the lyophilized polypeptide are stable and are suitable for storage, e.g., suitable for storage for long periods of time. Such storage may be at ambient conditions, may be under controlled temperature, may be under controlled humidity, or other condition or set of conditions; and may be stored in a sealed container (e.g., a bottle or jar with a removable lid, a tubes, a capsule, a caplet, a vial, syringe, dual-cartridge-syringe, or other container), and may be in a sealed container under an inert gas (e.g., nitrogen, argon, helium, or other inert gas), or other container with or without other element or compound in the container.

It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a polypeptide" includes a combination of two or more polypeptides, and the like.

"About" as used herein when referring to a measurable value such as an amount, a temporal duration, and the like, is meant to encompass variations of ±20% or ±10%, including ±5%, ±1%, and ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

All "amino acid" residues identified herein are in the natural L-configuration. In keeping with standard polypeptide nomenclature, abbreviations for amino acid residues are as shown in the following table.

| 1 Letter | 3 Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine. |

It should be noted that all amino acid residue sequences are represented herein by formulae whose left to right orientation is in the conventional direction of amino-terminus to carboxy-terminus.

In certain embodiments the volatile additive is an organic solvent. In one embodiment the organic solvent comprises a lower oxyhydrocarbon, a lower halohydrocarbon, a lower haloxyhydrocarbon, a lower sulfoxyhydrocarbon, a lower cyclohydrocarbon or combination thereof. In one embodiment the lower oxyhydrocarbon is methanol, ethanol, n-propanol, iso-propanol, n-butanol, iso-butanol, 2-butanol, t-butanol, pentanol, iso-pentanol, 2-pentanol, 3-pentanol, t-pentanol, methylethylketone, benzylalcohol, acetic acid, methylethyl ketone, or a combination thereof.

In certain embodiments the volatile additive is acetonitrile, ammonium acetate, or ammonium carbonate. In one embodiment the amount of ammonium acetate or ammonium carbonate is about 50 mM to about 300 mM. In one embodiment the amount of ammonium acetate or ammonium carbonate is about 100 mM or about 250 mM.

"Lower oxyhydrocarbons" as referred to herein means compounds possessing hydrocarbyl radicals and oxygen atoms having from 1 to 8 carbon atoms and from 1 to 4 oxygen atoms. Exemplary lower oxyhydrocarbons include, but are not limited to, lower alkanols, lower ketones, lower carboxylic acids, lower carboxylic esters, lower carbonates, and the like.

"Lower" as it refers to chemical compounds described herein refers to those compounds that have from 1 to 8 carbon atoms.

"Lower alkanol" refers to a saturated $C_1$-$C_8$ alkyl group which can be branched or straight-chained with from 1 to 4 hydroxyl groups. Exemplary lower alkanols having 1 hydroxyl group include, but are not limited to, methanol, ethanol, n-propanol, iso-propanol, n-butanol, iso-butanol, 2-butanol, t-butanol, pentanol, iso-pentanol, 2-pentanol, 3-pentanol, t-pentanol, and the like.

Exemplary "lower ketones" include, but are not limited to, acetone, methyl ethyl ketone, methyl propyl ketone, methyl isopropyl ketone, methyl butyl ketone, methyl isobutyl ketone, methyl 2-butyl ketone, methyl t-butyl ketone, diethyl ketone, ethyl propyl ketone, ethyl isopropyl ketone, ethyl butyl ketone, ethyl iso-butyl ketone, ethyl t-butyl ketone, and the like.

Exemplary "lower carboxylic acids" include, but are not limited to, formic acid, acetic acid, propionic acid, butyric acid isobutyric acid and the like.

Exemplary "lower carboxylic esters" include, but are not limited to, methyl acetate, ethyl acetate, propyl acetate, isopropyl acetate, butyl acetate, isobutyl acetate, 2-butyl acetate, t-butyl acetate, and the like.

Exemplary "lower carbonates" include, but are not limited to, dimethyl carbonate, methyl ethyl carbonate, methyl propyl carbonate, methyl isopropyl carbonate, methyl butyl carbonate, methyl iso-butyl carbonate, methyl 2-butyl carbonate, methyl t-butyl carbonate, diethyl carbonate, ethyl propyl carbonate, ethyl isopropyl carbonate, ethyl butyl carbonate, ethyl iso-butyl carbonate, ethyl t-butyl carbonate, and the like.

"Lower halohydrocarbons" as referred to herein means compounds possessing hydrocarbyl radicals and halo atoms having from 1 to 8 carbon atoms and from 1 to 4 halo atoms. Preferably, the halo atoms are chloro, fluoro and bromo. Most preferably, the halo atoms are chloro atoms. Exemplary lower halohydrocarbons, include, but are not limited to, methyl chloride, methylene chloride, chloroform, carbon tetrachloride, and the like.

"Lower haloxyhydrocarbons" means oxyhydrocarbons as defined herein which are further substituted with from 1 to 4 halo atoms. An exemplary haloxyhydrocarbon includes, but is not limited to, hexafluoroacetone.

"Lower sulfoxyhydrocarbons" means oxyhydrocarbons as defined herein which also contain a sulfur atom. Exemplary lower sulfoxyhydrocarbons include, but are not limited to, dimethyl sulfoxide (DMSO) and dimethyl sulfone.

"Lower cyclohydrocarbons" refers to hydrocarbyl radicals which are cyclized such as, for example, 3- to 8-member hydrocarbon rings. An exemplary cyclohydrocarbon includes, but is not limited to, cyclohexane.

"Polypeptide," "peptide" and "protein" are used interchangeably herein to refer to a polymer of amino acid residues. A polypeptide can be of natural (tissue-derived) origins, recombinant or natural expression from prokaryotic or eukaryotic cellular preparations, or produced chemically via synthetic methods. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine: D-(trifluoromethyl)-phenylglycine; D-(trifluoromethyl)-phenylalanine: D-p-fluoro-phenylalanine; D- or L-p-biphenylphenylalanine; K- or L-p-methoxy-biphenylphenylalanine: D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" as used herein includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. "Cationic" as used herein refers to any peptide that possesses a net positive charge at pH 7.4. The biological activity of the peptides can be determined by standard methods known to those of skill in the art and described herein.

"Recombinant" when used with reference to a protein indicates that the protein has been modified by the introduction of a heterologous nucleic acid or protein or the alteration of a native nucleic acid or protein.

As used "reconstitution time" and grammatical variations thereof means the amount of time necessary for a lyophilized molecule to be dissolved and/or suspended in a liquid form. For instance, reconstitution time includes, but it not limited to the time required for a dried pellet of polypeptide to become suspended in water or a buffer after lyophilization. Accordingly, a "reduction" or "reducing" reconstitution time and grammatical variations thereof, means less time is required for polypeptide dried under a first formulation and/or condition to suspend in a liquid compared with the same polypeptide dried under a second formulation and/or condition and suspended in the same liquid.

The present invention is also directed to a method for reducing the reconstitution time of a lyophilized polypeptide composition comprising: a) lyophilizing a liquid mixture comprising the polypeptide, wherein the liquid mixture comprises a volatile additive and b) reconstituting the lyophilized polypeptide with a sufficient amount of a pharmaceutically acceptable dispersing agent to the lyophilized polypeptide composition to yield a liquid polypeptide composition, wherein time for reconstituting the polypeptide lyophilized in the presence of the volatile additive is less than the time for reconstituting the same polypeptide lyophilized in the absence of the volatile additive.

The present invention is also directed to a method for producing a liquid polypeptide composition comprising: obtaining a lyophilized polypeptide produced by a method of the present invention, and reconstituting the lyophilized polypeptide with a sufficient amount of a pharmaceutically acceptable dispersing agent to yield a liquid polypeptide composition. The present invention is also directed to a liquid polypeptide composition produced by a method of the present invention.

In certain exemplary embodiments, the lyophilized polypeptide readily reconstitutes once contacted with a sufficient amount of a pharmaceutically acceptable dispersing agent. For example, in certain embodiments, the lyophilized polypeptide is mixed, e.g., shaken for about 5 seconds and then allowed to stand for about 5 to about 30 minutes, with a dispersing agent to provide a liquid polypeptide composition. The dispersing agent is preferably sterile water or "water for injection" (WFI). The liquid polypeptide can be further diluted with isotonic saline or other excipients to produce a desirable concentration prior to administration. According to the present invention, "excipients" includes, but is not limited to, stabilizers, for example, human serum albumin (hsa), bovine serum albumin (bsa), α-casein, globulins, α-lactalbumin, LDH, lysozyme, myoglobin, ovalbumin, RNase A; buffering agents, for example, citric acid, HEPES, histidine, potassium acetate, postassium citrate, potassium phosphate ($KH_2PO_4$), sodium acetate, sodium bicarbonate, sodium citrate, sodium phosphate ($NAH_2PO_4$), Tris base, and Tris-HCl; amino acids/metabolites, for example, glycine, alanine (α-alanine, β-alanine), arginine, betaine, leucine, lysine, glutamic acid, aspartic acid, histidine, proline, 4-hydroxyproline, sarcosine, γ-aminobutyric acid (GABA), opines (alanopine, octopine, strombine), and trimethylamine N-oxide (TMAO); surfactants, for example, polysorbate 20 and 80, and poloxamer 407: fatty acids, for example, phosphotidyl choline, ethanolamine, and acethyl-tryptophanate: polymers, for example, polyethylene glycol (PEG), and polyvinylpyrrolidone (PVP) 10, 24, 40; low molecular weight excipients, for example, arabinose, cellobiose, ethylene glycol, fructose, fucose, galactose, glycerin/glycerol, glucose, innositol, lactose, mannitol, maltose, maltotriose, mannose, melibiose, 2-methyl-2,4-pentanediol, octulose, propylene glycol, raffinose, ribose, sorbitol, sucrose, trehalose, xylitol, and xylose; and high molecular weight excipients, for example, cellulose, β-cyclodextrin, dextran (10 kd), dextran (40 kd), dextran (70 kd), ficoll, gelatin, hydroxypropylmethyl-cellulose, hydroxyethyl starch, maltodextrin, methocel, peg (6 kd), polydextrose, polyvinylpyrrolidone (PVP) k15 (10 kd), PVP (40 kd), PVP k30 (40 kd), PVP k90 (1000 kd), sephadex G 200, and starch; antioxidants, for example, ascorbic acid, cysteine HCl, thioglycerol, thioglycolic acid, thiosorbitol, and glutathione; reducing agents, for example, cysteine HCl, dithiothreotol, and other thiol or thiophenes; chelating agents, for example, EDTA, EGTA, glutamic acid, and aspartic acid; inorganic salts/metals, for example, $Ca^{2+}$, $Ni^{2+}$, $Mg^{2+}$, $Mn^{2+}$, $Na_2SO_4$, $(NH_4)_2SO_4$, $Na_2HPO_4/NaH_2PO_4$, $K_2HPO_4/KH_2PO_4$, $MgSO_4$, and NaF; organic salts, for example, Na acetate, Na polyethylene, Na caprylate (Na octanoate), proprionate, lactate, succinate, and citrate; organic solvents, for example, acetonitrile, dimethylsulfoxide (dmso), and ethanol.

In exemplary embodiments of the present invention, the liquid polypeptide compositions that are produced exhibit desirable characteristics, such as desirable viscosity and surface tension characteristics.

The term "surface tension" refers to the attractive force exerted by the molecules below the surface upon those at the surface/air interface, resulting from the high molecular concentration of a liquid compared to the low molecular concentration of the gas. Liquids with low values of surface tension, such as nonpolar liquids, flow more readily than water. Typically, values of surface tensions are expressed in newtons/meters or dynes/centimeters.

"Dynamic surface tension" as referred to herein is the surface/air interface and the dynamic interfacial tension to the surface/surface interface. There are a number of alternative methods for measuring dynamic surface tension, for example, captive bubble surface tensionometry or pulsating bubble surface tensionometry.

The term "viscosity" refers to the internal resistance to flow exhibited by a fluid at a specified temperature; the ratio of shearing stress to rate of shear. A liquid has a viscosity of one poise if a force of 1 dyne/square centimeter causes two parallel liquid surfaces one square centimeter in area and one square centimeter apart to move past one another at a velocity of 1 cm/second. One poise equals one hundred centipoise.

When referring to apparent viscosity, it is understood that the value of viscosity is dependent on the conditions under which the measurement was taken, such as temperature, the rate of shear and the shear stress employed. The apparent viscosity is defined as the ratio of the shear stress to the rate of shear applied. There are a number of alternative methods for measuring apparent viscosity. For example, viscosity can be tested by a suitable cone and plate, parallel plate or other type of viscometer or rheometer.

The present invention is also directed to a formulation suitable for lyophilization of a polypeptide. In certain embodiments the liquid mixture comprises from about 0.1% by volume to about 10% by volume of volatile additive, from about 0.25% by volume to about 5% by volume of volatile additive, or about 2% by volume of volatile additive. In one embodiment the formulation comprises about 10 mM sodium phosphate, pH 7.2, about 117 mM trehalose, about 153 mM mannitol, and about 0.01% (w/v) polysorbate-80. In another embodiment, the formulation comprises 26 mM histidine, 150 mM trehalose, 0.02% polysorbate 80 (PS80), pH 6.0. In certain embodiments the polypeptide comprises albiglutide (SEQ ID NO:1). In other embodiments the polypeptide comprises IL18 (SEQ ID NO: 6). In one embodiment, the present invention is directed to a liquid formulation comprising about 2% t-butanol. In one embodiment the liquid formulation comprises about 2% t-butanol, about 10 mM sodium phosphate, pH 7.2, about 117 mM trehalose, about 153 mM mannitol, and about 0.01% (w/v) polysorbate-80. In another embodiment, the formulation comprises about 2% t-butanol, about 26 mM histidine, pH 6.0, about 150 mM trehalose, and about 0.02% polysorbate 80 (PS80).

As used herein a "therapeutic protein" refers to any protein and/or polypeptide that can be administered to a mammal to elicit a biological or medical response of a tissue, system, animal or human that is being sought, for instance, by a researcher or clinician. A therapeutic protein may elicit more than one biological or medical response. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

In one aspect, the present invention is directed to a composition comprising: a therapeutic polypeptide, a buffer, a surfactant, at least one excipient, and at least one volatile additive. In one embodiment, the therapeutic polypeptide comprises GLP-1 or a fragment and/or variant thereof. In one embodiment, the therapeutic polypeptide comprises at least two GLP-1(7-36(A8G)) polypeptides genetically fused to the N-terminus of human serum albumin. In one embodiment, the therapeutic polypeptide comprises SEQ ID NO:1.

In one embodiment, the therapeutic protein comprises a GLP-1 agonist. In one embodiment, the therapeutic protein comprises human serum albumin.

In one aspect, the present invention is directed to use of any one of the compositions of claims of the present invention for making a medicament comprising SEQ ID NO:1.

In one embodiment, the buffer is sodium phosphate. In one embodiment the buffer is histidine.

In one embodiment, the surfactant is polysorbate-80. In one embodiment, the at least one excipient is selected from: trehalose, maltose, sucrose, mannose, lactose, mannitol, sorbitol, glycerol and dextrose. In one embodiment, the excipient comprises: trehalose and mannitol.

"GLP-1 agonist" as used herein means any compound or composition capable of simulating insulin production and/or having at least one GLP-1 activity including, but not limited to an incretin hormone and/or fragment, variant and/or conjugate thereof and an incretin mimetic and/or fragment, variant and/or conjugate thereof.

"Incretin hormone" as used herein means any hormone that potentiates insulin secretion or otherwise raises the level or insulin. One example of an incretin hormone is GLP-1. GLP-1 is an incretin secreted by intestinal L cells in response to ingestion of food. In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying time and slows small bowel motility delaying food absorption. GLP-1 promotes continued beta cell competence by stimulating transcription of genes involved in glucose dependent insulin secretion and by promoting beta-cell neogenesis (Meier, et al. Biodrugs 2003; 17 (2): 93-102).

"GLP-1 activity" as used herein means one or more of the activities of naturally occurring human GLP-1, including but not limited to, reducing blood and/or plasma glucose, stimulating glucose-dependent insulin secretion or otherwise raising the level of insulin, suppressing glucagon secretion, reducing fructosamine, increases glucose delivery and metabolism to the brain, delaying gastric emptying, and promoting beta cell competence, and/or neogenesis. Any of these activities and other activity associated with GLP-1 activity may be caused directly or indirectly by a composition having GLP-1 activity or a GLP-1 agonist. By way of example, a composition having GLP-1 activity may directly or indirectly stimulate glucose-dependent insulin production while the stimulation of insulin production may indirectly reduce plasma glucose levels in a mammal.

An "incretin mimetic" as used herein is a compound capable of potentiating insulin secretion or otherwise raise the level of insulin. An incretin mimetic may be capable of stimulating insulin secretion, increasing beta cell neogenesis, inhibiting beta cell apoptosis, inhibiting glucagon secretion, delaying gastric emptying and inducing satiety in a mammal. An incretin mimetic may include, but is not limited to, any polypeptide which has GLP-1 activity, including but not limited to, exendin 3 and exendin 4, including any fragments and/or variants and/or conjugates thereof.

As used herein "conjugate" or "conjugated" and grammatical variations thereof refer to two molecules that are bound to each other. For example, a first polypeptide may be covalently or non-covalently bound to a second polypeptide. The first polypeptide may be covalently bound by a chemical linker or may be genetically fused to the second polypeptide, wherein the first and second polypeptide share a common polypeptide backbone.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants may also include, but are not limited to, polypeptides or fragments thereof having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

In one embodiment of the present invention, the polypeptide is a GLP-1 polypeptide. "GLP-1 polypeptide" includes, but is not limited to, GLP-1 or a fragment, variant, and/or conjugate thereof. GLP-1 fragments and/or variants and/or conjugates of the present invention typically have at least one GLP-1 activity. A GLP-1 or a fragment, variant, and/or conjugate thereof may comprise human serum albumin. Human serum albumin may be conjugated to the GLP-1 or fragment and/or variant thereof. Human serum albumin may be conjugated to an incretin hormone (such as GLP-1) and/or incretin mimetic (such as exendin 3 and exendin 4) and/or fragments and/or variants thereof through a chemical linker prior to injection or may be chemically linked to naturally occurring human serum albumin in vivo (see for instance, U.S. Pat. No. 6,593,295 and U.S. Pat. No. 6,329, 336, herein incorporated by reference in their entirety). Alternatively, human serum albumin may be genetically fused to a GLP-1 and/or fragment and/or variant thereof or other GLP-1 agonist such as exendin-3 or exendin-4 and/or fragments and/or variants thereof. Examples of GLP-1 and fragments and/or variants thereof genetically fused with human serum albumin are provided in the following PCT applications: WO 2003/060071, WO 2003/59934, WO 2005/003296, WO 2005/077042 (herein incorporated by reference in their entirety).

Polypeptides having GLP-1 activity may comprise at least one fragment and/or variant of human GLP-1. The two naturally occurring fragments of human GLP-1 are represented in SEQ ID NO: 2.

```
                                         (SEQ ID NO.: 2)
 7   8   9  10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Xaa
``` wherein: Xaa at position 37 is Gly (hereinafter designated as "GLP-1(7-37)"), or —NH$_2$ (hereinafter designated as "GLP-1(7-36)"). GLP-1 fragments may include, but are not limited to, molecules of GLP-1 comprising, or alternatively consisting of, amino acids 7 to 36 of human GLP-1 (GLP-1(7-36)). Variants of GLP-1 or fragments thereof may include, but are not limited to, one, two, three, four, five or more amino acid substitutions in wild type GLP-1 or in the naturally occurring fragments of GLP-1 shown in SEQ ID NO.: 2. Variants GLP-1 or fragments of GLP-1 may include, but are not limited to, substitutions of an alanine residue analogous to alanine 8 of wild type GLP-1, such alanine being mutated to a glycine (hereinafter designated as "A8G") (See for example, the mutants disclosed in U.S. Pat. No. 5,545,618, herein incorporated by reference in its entirety).

In some aspects, at least one fragment and variant of GLP-1 comprises GLP-1(7-36(A8G)) and is genetically fused to human serum albumin. In a further embodiment, polypeptides of the invention comprise one, two, three, four, five, or more tandemly oriented molecules of GLP-1 and/or fragments and/or variants thereof fused to the N- or C-terminus of human serum albumin or variant thereof. Other embodiments have such A8G polypeptides fused to the N- or C-terminus of albumin or variant thereof. An example of two tandemly oriented GLP-1(7-36)(A8G) fragments and/or variants fused to the N-terminus of human serum albumin comprises SEQ ID NO:1, which is presented in FIG. 3. In another aspect, at least one fragment and variant of GLP-1 comprises at least two GLP-1(7-36(A8G)) tandemly and genetically fused to the human serum albumin. In one aspect, at least two GLP-1(7-36(A8G)) are genetically fused at the N-terminus of the human serum albumin. At least one polypeptide having GLP-1 activity can comprise SEQ ID No.: 1.

Variants of GLP-1(7-37) may be denoted for example as Glu$^{22}$-GLP-1(7-37)OH which designates a GLP-1 variant in which the glycine normally found at position 22 of GLP-1(7-37)OH has been replaced with glutamic acid; Val$^{8}$-Glu$^{22}$-GLP-1(7-37)OH designates a GLP-1 compound in which alanine normally found at position 8 and glycine normally found at position 22 of GLP-1(7-37)OH have been replaced with valine and glutamic acid, respectively. Examples of variants of GLP-1 include, but are not limited to,

| | | |
|---|---|---|
| Val$^{8}$-GLP-1(7-37)OH | Gly$^{8}$-GLP-1(7-37)OH | Glu$^{22}$-GLP-1(7-37)O-H |
| Asp$^{22}$-GLP-1(7-37)OH | Arg$^{22}$-GLP-1(7-37)OH | Lys$^{22}$-GLP-1(7-37)OH |
| Cys$^{22}$-GLP-1(7-37)OH | Val$^{8}$-Glu$^{22}$-GLP-1(7-37)OH | Val$^{8}$-Asp$^{22}$-GLP-1(7-37)OH |
| Val$^{8}$-Arg$^{22}$-GLP-1(7-37)OH | Val$^{8}$-Lys$^{22}$-GLP-1(7-37)OH | Val$^{8}$-Cys$^{22}$-GLP-1(7-37)OH |
| Gly$^{8}$-Glu$^{22}$-GLP-1(7-37)OH | Gly$^{8}$-Asp$^{22}$-GLP-1(7-37)OH | Gly$^{8}$-Arg$^{22}$-GLP-1(7-37)OH |
| Gly$^{8}$-Lys$^{22}$-GLP-1(7-37)OH | Gly$^{8}$-Cys$^{22}$-GLP-1(7-37)OH | Glu$^{22}$-GLP-1(7-36)OH |
| Asp$^{22}$-GLP-1(7-36)OH | Arg$^{22}$-GLP-1(7-36)OH | Lys$^{22}$-GLP-1(7-36)OH |
| Cys$^{22}$-GLP-1(7-36)OH | Val$^{8}$-Glu$^{22}$-GLP-1(7-36)OH | Val$^{8}$-Asp$^{22}$-GLP-1(7-36)OH |
| Val$^{8}$-Arg$^{22}$-GLP-1(7-36)OH | Val$^{8}$-Lys$^{22}$-GLP-1(7-36)OH | Val$^{8}$-Cys$^{22}$-GLP-1(7-36)OH |
| Gly$^{8}$-Glu$^{22}$-GLP-1(7-36)OH | Gly$^{8}$-Asp$^{22}$-GLP-1(7-36)OH | Gly$^{8}$-Arg$^{22}$-GLP-1(7-36)OH |
| Gly$^{8}$-Lys$^{22}$-GLP-1(7-36)OH | Gly$^{8}$-Cys$^{22}$-GLP-1(7-36)OH | Lys$^{23}$-GLP-1(7-37)OH |
| Val$^{8}$-Lys$^{23}$-GLP-1(7-37)OH | Gly$^{8}$-Lys$^{23}$-GLP-1(7-37)OH | His$^{24}$-GLP-1(7-37)OH |
| Val$^{8}$-His$^{24}$-GLP-1(7-37)OH | Gly$^{8}$-His$^{24}$-GLP-1(7-37)OH | Lys$^{24}$-GLP-1(7-37)OH |
| Val$^{8}$-Lys$^{24}$-GLP-1(7-37)OH | Gly$^{8}$-Lys$^{23}$-GLP-1(7-37)OH | Glu$^{30}$-GLP-1(7-37)OH |
| Val$^{8}$-Glu$^{30}$-GLP-1(7-37)OH | Gly$^{8}$-Glu$^{30}$-GLP-1(7-37)OH | Asp$^{30}$-GLP-1(7-37)OH |
| Val$^{8}$-Asp$^{30}$-GLP-1(7-37)OH | Gly$^{8}$-Asp$^{30}$-GLP-1(7-37)OH | Gln$^{30}$-GLP-1(7-37)OH |
| Val$^{8}$-Gln$^{30}$-GLP-1(7-37)OH | Gly$^{8}$-Gln$^{30}$-GLP-1(7-37)OH | Tyr$^{30}$-GLP-1(7-37)OH |

-continued

| | | |
|---|---|---|
| Val$^8$-Tyr$^{30}$-GLP-1(7-37)OH | Gly$^8$-Tyr$^{30}$-GLP-1(7-37)OH | Ser$^{30}$-GLP-1(7-37)OH |
| Val$^8$-Ser$^{30}$-GLP-1(7-37)OH | Gly$^8$-Ser$^{30}$-GLP-1(7-37)OH | His$^{30}$-GLP-1(7-37)OH |
| Val$^8$-His$^{30}$-GLP-1(7-37)OH | Gly$^8$-His$^{30}$-GLP-1(7-37)OH | Glu$^{34}$-GLP-1(7-37)OH |
| Val$^8$-Glu$^{34}$-GLP-1(7-37)OH | Gly$^8$-Glu$^{34}$-GLP-1(7-37)OH | Ala$^{34}$-GLP-1(7-37)OH |
| Val$^8$-Ala$^{34}$-GLP-1(7-37)OH | Gly$^8$-Ala$^{34}$-GLP-1(7-37)OH | Gly$^{34}$-GLP-1(7-37)OH |
| Val$^8$-Gly$^{34}$-GLP-1(7-37)OH | Gly$^8$-Gly$^{34}$-GLP-1(7-37)OH | Ala$^{35}$-GLP-1(7-37)OH |
| Val$^8$-Ala$^{35}$-GLP-1(7-37)OH | Gly$^8$-Ala$^{35}$-GLP-1(7-37)OH | Lys$^{35}$-GLP-1(7-37)OH |
| Val$^8$-Lys$^{35}$-GLP-1(7-37)OH | Gly$^8$-Lys$^{35}$-GLP-1(7-37)OH | His$^{35}$-GLP-1(7-37)OH |
| Val$^8$-His$^{35}$-GLP-1(7-37)OH | Gly$^8$-His$^{35}$-GLP-1(7-37)OH | Pro$^{35}$-GLP-1(7-37)OH |
| Val$^8$-Pro$^{35}$-GLP-1(7-37)OH | Gly$^8$-Pro$^{35}$-GLP-1(7-37)OH | Glu$^{35}$-GLP-1(7-37)OH |
| Gly$^8$-Glu$^{35}$-GLP-1(7-37)OH | Val$^8$-Ala$^{27}$-GLP-1(7-37)OH | Val$^8$-His$^{37}$-GLP-1(7-37)OH |
| Val$^8$-Glu$^{22}$-Lys$^{23}$-GLP-1(7-37)OH | Val$^8$-Glu$^{22}$-Glu$^{23}$-GLP-1(7-37)OH | Val$^8$-Glu$^{22}$-Ala$^{27}$-GLP-1(7-37)OH |
| Val$^8$-Gly$^{34}$-Lys$^{35}$-GLP-1(7-37)OH | Val$^8$-His$^{37}$-GLP-1-(7-37)OH | Gly$^8$-His$^{37}$-GLP-1(7-37)OH |
| Val$^8$-Glu$^{22}$-Ala$^{27}$-GLP-1(7-37)OH | Gly$^8$-Glu$^{22}$-Ala$^{27}$-GLP-1(7-37)OH | Val$^8$-Lys$^{22}$-Glu$^{23}$-GLP-1(7-37)OH |
| Gly$^8$-Lys$^{22}$-Glu$^{23}$-GLP-1(7-37)OH. | Val$^8$-Glu$^{35}$-GLP-1(7-37)OH | |

Variants of GLP-1 may also include, but are not limited to, GLP-1 or GLP-1 fragments having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

GLP-1 fragments or variants may also include polypeptides in which one or more amino acids have been added to the N-terminus and/or C-terminus of GLP-1(7-37)OH of the fragment or variant. The amino acids in GLP-1 in which amino acids have been added to the N-terminus or C-terminus are denoted by the same number as the corresponding amino acid in GLP-1(7-37)OH. For example, the N-terminus amino acid of a GLP-1 compound obtained by adding two amino acids to the N-terminus of GLP-1(7-37)OH is at position 5; and the C-terminus amino acid of a GLP-1 compound obtained by adding one amino acid to the C-terminus of GLP-1(7-37)OH is at position 38. Thus, position 12 is occupied by phenylalanine and position 22 is occupied by glycine in both of these GLP-1 compounds, as in GLP-1(7-37)OH. Amino acids 1-6 of a GLP-1 with amino acids added to the N-terminus may be the same as or a conservative substitution of the amino acid at the corresponding position of GLP-1(1-37)OH. Amino acids 38-45 of a GLP-1 with amino acids added to the C-terminus may be the same as or a conservative substitution of the amino acid at the corresponding position of glucagon or exendin-4.

Albiglutide is a novel analogue of GLP-1 synthesized through genetic fusion of a DPP-IV resistant form of the peptide as a dimer to human albumin, which provides a long-lasting GLP-1 activity with a half-life of about 5 to 7 days. The primary amino acid sequence of albiglutide is SEQ ID NO.:1.

In another aspect of the present invention, the composition comprising at least one polypeptide having GLP-1 activity is administered to a human from once daily to once every month and can be administered once daily, once every two days, once every three days, once every seven days, once every fourteen days, once every four weeks and/or once every month. In another aspect, a first dose and a second dose of a composition comprising at least one polypeptide having GLP-1 activity is administered to a human. The first and the second dose can be the same or can be different. Each dose of least one polypeptide having GLP-1 activity can comprise about 0.25 μg to about 1000 mg of the at least one polypeptide having GLP-1 activity. Doses can include, but are not limited to, 0.25 μg, 0.25 mg, 1 mg, 3 mg, 6 mg, 16 mg, 24 mg 48 mg, 60 mg, 80 mg, 104 mg, 20 mg, 400 mg. 800, mg up to about 1000 mg of the at least one polypeptide having GLP-1 activity.

In one embodiment, compositions of the present invention comprise about 15 mg, 30 mg, 50 mg or 100 mg of SEQ ID NO:1.

In another embodiment the polypeptide is an antigen binding polypeptide. In one embodiment the antigen binding polypeptide is selected from the group consisting of a soluble receptor, antibody, antibody fragment, immunoglobulin single variable domain, Fab, F(ab')2, Fv, disulphide linked Fv, scFv, closed conformation multispecific antibody, disulphide-linked scFv, or diabody.

The term "antigen binding polypeptide" as used herein refers to antibodies, antibody fragments and other protein constructs which are capable of binding to an antigen.

In one embodiment the antigen binding polypeptide is an anti-NOGO mAb. In one embodiment the antigen binding polypeptide comprises heavy chain of SEQ ID NO: 3 and the light chain of SEQ ID NO: 4.

In one embodiment the antigen binding polypeptide is an anti-IL5 mAb. In one embodiment the antigen binding polypeptide comprises heavy chain of SEQ ID NO: 7 and the light chain of SEQ ID NO: 8.

In one embodiment the antigen binding polypeptide is an anti-CD20 mAb. In one embodiment the antigen binding polypeptide comprises heavy chain variable region of SEQ ID NO: 9 and the light chain variable region of SEQ ID NO: 10. In one embodiment the antigen binding polypeptide is an immunoglobulin single variable domain. In one embodiment the immunoglobulin single variable domain is an anti-TNFR1 dAb. In one embodiment the immunoglobulin single variable domain comprises SEQ ID NO: 5.

The terms Fv, Fc, Fd, Fab, or F(ab)2 are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT™ database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see for example EP-A-0239400 and EP-A-054951.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. An "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, V) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid $V_{HH}$ dAbs (nanobodies). Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are still considered to be "domain antibodies" according to the invention. As used herein "$V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain.

As used herein, the term "antigen-binding site" refers to a site on a protein which is capable of specifically binding to antigen, this may be a single domain, for example an epitope-binding domain, or it may be paired $V_H/V_L$ domains as can be found on a standard antibody. In some aspects of the invention single-chain Fv (ScFv) domains can provide antigen-binding sites.

The terms "mAbdAb" and "dAbmAb" are used herein to refer to antigen-binding proteins of the present invention. The two terms can be used interchangeably, and are intended to have the same meaning as used herein.

EXAMPLES

The present invention may be further understood by reference to the following non-limiting examples.

Example 1—Lyophilization of Albiglutide in the Presence of t-Butanol, Ethanol, Acetonitrile, NH₄Acetate or NH₄HCO₃

Samples of albiglutide were prepared for lyophilization according to the analytical preparation matrix described in Table I. The lyophiles were prepared by lyophilizing 0.750 mL of solution containing 50 mg of albiglutide in 10 mM sodium phosphate, pH 7.2, with 117 mM trehalose, 153 mM mannitol, 0.01% (w/v) polysorbate-80 in vials (2 mL 13 mm) containing the appropriate concentration of t-butanol, ethanol, and acetonitrile (1, 5, and 10% w/v); and the appropriate concentration of NH₄Acetate and NH₄HCO₃ (100 mM and 250 mM).

TABLE 1

Albiglutide conditions as a function of sample number.

| # Conditions | Shake/Rest Recon (min) | Fold-change | Undisturbed Recon (min) | Fold-change |
|---|---|---|---|---|
| 1: Form. Buffer | 7.18 (+/−0.75) | N.A. | 18.09 (+/−4.55) | |
| 2: 1% tButanol | 3.23 (+/−0.43) | 0.45 | 6.01 (+/−1.56) | 0.33 |
| 3: 5% tButanol | 5.38 (+/−0.44) | 0.75 | 9.18 (+/−4.57) | 0.51 |
| 4: 10% tButanol | 4.06 (+/−0.56) | 0.57 | 4.80 (+/−0.10) | 0.27 |
| 5: 1% Ethanol | 6.17 (+/−0.67) | 0.86 | 14.89 (+/−2.83) | 0.82 |
| 6: 5% Ethanol | 6.85 (+/−0.61) | 0.95 | 13.47 (+/−0.56) | 0.74 |
| 7: 10% Ethanol | 5.78 (+/−0.55) | 0.81 | 11.01 (+/−0.83) | 0.61 |
| 8: 1% Acetonitrile | 5.90 (+/−0.55) | 0.82 | 13.22 (+/−0.60) | 0.73 |
| 9: 5% Acetonitrile | 6.05 (+/−0.53) | 0.84 | 12.60 (+/−1.64) | 0.70 |
| 10: 10% Acetonitrile | 5.82 (+/−0.51) | 0.81 | 10.27 (+/−0.11) | 0.57 |
| 11: 100 mM NH4Acetate | 7.81 (+/−0.51) | 1.09 | 10.73 (+/−0.59) | 0.59 |
| 12: 250 mM NH4Acetate | 6.65 (+/−0.90) | 0.93 | 10.98 (+/−3.22) | 0.61 |
| 13: 100 mM NH4HCO3 | 6.55 (+/−0.56) | 0.91 | 10.63 (+/−2.26) | 0.59 |
| 14: 250 mM NH4HCO3 | 6.72 (+/−0.20) | 0.94 | 9.95 (+/−1.85) | 0.55 |
| | (n = 5) | | (n = 3) | |

The samples were lyophilized using a LyoStar freeze dryer under the following cycling conditions:

| 74 hr Cycle Stage | Time (min) | Temp | Pressure |
|---|---|---|---|
| Load | 0 | 5° C. | Atmospheric |
| | 60 | 5° C. | Atmospheric |
| Ramp to Freeze | 180 | −55° C. | Atmospheric |
| Freeze | 300 | −55° C. | Atmospheric |
| Ramp to Anneal | 360 | −15° C. | Atmospheric |
| Anneal | 660 | −15° C. | Atmospheric |
| Ramp to 1° Dry | 780 | −55° C. | Atmospheric |
| Refreeze | 900 | −55° C. | Atmospheric |
| Pull Vacuum | 930 | −55° C. | 100 um Hg |
| 1° Dry | 1050 | −55° C. | 100 um Hg |
| Ramp to 1° Dry | 1170 | −25° C. | 100 um Hg |
| 1° Dry | 3570 | −25° C. | 100 um Hg |
| Ramp to 2° Dry | 3930 | 40° C. | 100 um Hg |
| 2° Dry | 4350 | 40° C. | 100 um Hg |
| 2 hr Ramp to RT | 4470 | 25° C. | 100 um Hg |
| Hold at RT | 4650 | 25° C. | 100 um Hg |
| | 74.5 | | |

Example 2—Reconstitution of Lyophilized Albiglutide

Figure 2:
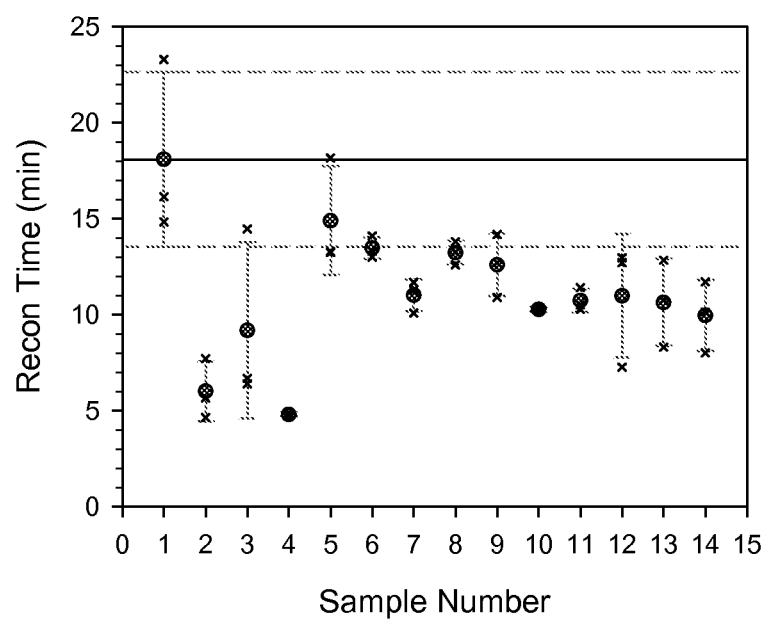
FIG. 2. Plots of lyophile reconstitution times using undisturbed method.

The lyophiles were reconstituted with 0.675 mL water for injection (WFI) via a 1 mL syringe and 25 G(⅝") needle through the lyophilized vial stopper (tuberculin syringes, Becton-Dickinson#309626). The volume of 0.675 mL corrects for the volume of the dry components resulting in a final volume of 0.75 mL. The reconstitution was performed using either a "shaking method" or an "undisturbed method". For the shaking method, the sample was shaken for 10 seconds, followed by 15 seconds of rest. For the undisturbed method, the sample was rocked back and forth for 5 seconds and then left undisturbed. The samples were considered to have been reconstituted when no particles were visible in the vials. Results for both reconstitution methods are shown in Table 1 and also in FIGS. 1 and 2.

Example 3—Lyophilization of Albiglutide in the Presence of t-Butanol

Samples of albiglutide were prepared for lyophilization according to the analytical preparation matrix described in Table I. The lyophiles were prepared by lyophilizing 0.750 mL of solution containing 50 mg of albiglutide in 10 mM sodium phosphate, pH 7.2, with 117 mM trehalose, 153 mM mannitol, 0.01% (w/v) polysorbate-80 in vials (2 mL 13 mm) containing the appropriate concentration of t-butanol (between 34 and 202 mM, or 0.25 to 2% w/v).

TABLE 2

Albiglutide conditions as a function of sample number.

| Sample # | 6 Conditions: | Vials/ Cond. | Vol. of 100 mg/mL BDS (mL) |
|---|---|---|---|
| 1 | albiglutide control | 52 | 45.0 (0.75 mL/vial) |
| 2 | 2% t-Butanol | 42 | 37.5 (0.76 mL/vial) |
| 3 | 1.5% t-Butanol | 42 | 37.5 (0.76 mL/vial) |
| 4 | 1% t-Butanol | 52 | 45.0 (0.76 mL/vial) |
| 5 | 0.5% t-Butanol | 42 | 37.5 (0.75 mL/vial) |
| 6 | 0.25% t-Butanol | 42 | 37.5 (0.75 mL/vial) |

The samples were lyophilized using a LyoStar freeze dryer under the following cycling conditions:

| 74 hr Cycle Stage | Time (min) | Temp | Pressure |
|---|---|---|---|
| Load | 0 | 5° C. | Atmospheric |
|  | 60 | 5° C. | Atmospheric |
| Ramp to Freeze | 180 | −55° C. | Atmospheric |
| Freeze | 300 | −55° C. | Atmospheric |
| Ramp to Anneal | 360 | −15° C. | Atmospheric |
| Anneal | 660 | −15° C. | Atmospheric |
| Ramp to 1° Dry | 780 | −55° C. | Atmospheric |
| Refreeze | 900 | −55° C. | Atmospheric |
| Pull Vacuum | 930 | −55° C. | 100 um Hg |
| 1° Dry | 1050 | −55° C. | 100 um Hg |
| Ramp to 1° Dry | 1170 | −25° C. | 100 um Hg |
| 1° Dry | 3570 | −25° C. | 100 um Hg |
| Ramp to 2° Dry | 3930 | 40° C. | 100 um Hg |
| 2° Dry | 4350 | 40° C. | 100 um Hg |
| 2 hr Ramp to RT | 4470 | 25° C. | 100 um Hg |
| Hold at RT | 4650 | 25° C. | 100 um Hg |
|  | 74.5 |  |  |

Example 4—Reconstitution of Lyophilized Albiglutide

The lyophiles were reconstituted with 0.675 mL water for injection (WFI) via a 1 mL syringe and 25 G(⅝") needle through the lyophilized vial stopper (tuberculin syringes, Becton-Dickinson#309626). The volume of 0.675 mL corrects for the volume of the dry components resulting in a final volume of 0.75 mL. The reconstitution was performed using an "undisturbed method" (addition of the water was followed by immediate light mixing followed by allowing the vial to stand undisturbed). Addition of the water was performed with four variations based on analyst (three different people performing the reconstitution step) and pipetting method:

Analyst 1: reconstitution via syringe through the stopper.
Analyst 2: reconstitution via syringe through the stopper.
Analyst 3: reconstitution via syringe through the stopper.
Analyst 1: reconstitution via traditional P1000 Rainin pipetting method.

Figure 3:
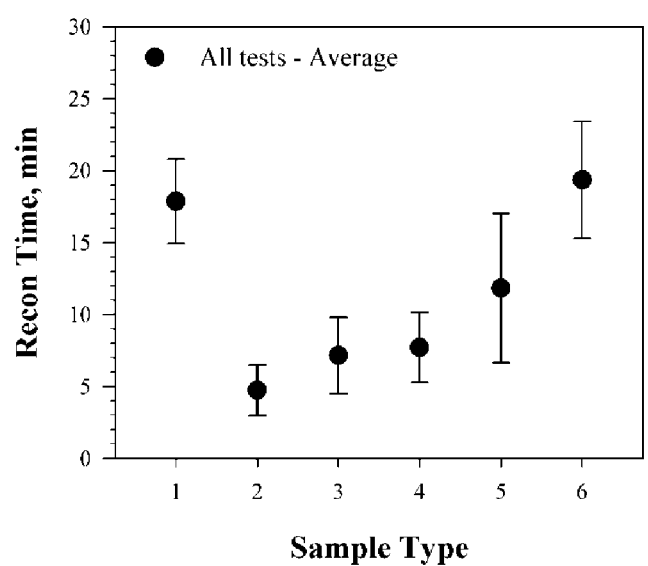
FIG. 3. Plots of lyophile reconstitution times as a function of sample number. (A) Box plots summarizing the average recon times over all tests as a function of sample number. The boundary of the box closest to zero indicates the 25th percentile, a line within the box marks the median, and the boundary of the box farthest from zero indicates the 75th percentile. Whiskers (error bars) above and below the box indicate the 90th and 10th percentile. Outliers below 10th or above 90th percentile are plotted as symbols. (B) All lyophile recon times plotted as a function of sample number.

Individual reconstitution times are summarized in Table 4, and graphically in FIG. 3. There is a clear effect of t-butanol added prior to lyophilization on the resulting reconstitution time endpoint values. The control samples were lyophilized in the presence of formulation buffer only (no volatile additive) and gave an average of t=17.87 (±2.94) min (n=26); the high and low values were t=12.25 min and t=26.53 min, respectively. The 0.25% t-Butanol samples were virtually identical to control samples, with a reconstitution endpoint average time of t=19.35 (±4.08) min (n=20); the high and low values were t=12.42 min and t=28.90 min, respectively.

At concentrations of t-butanol at 0.5% or above, there is a clear acceleration of reconstitution rates with endpoint values decreasing with increasing t-butanol concentrations. At 0.5% t-butanol, the average reconstitution time endpoint over all results was approximately 65% of the control group, with t=11.84 (±2.94) min (n=19); the high and low values were t=0.58 min and t=17.93, respectively. Note that one sample in the 0.5% group gave >37 min. In this case the lyophile stuck to the side of the vial above the solvent meniscus and failed to go into solution, thus the data point was excluded from averaging.

Comparing 1% t-butanol, 1.5% t-butanol, and 2% t-butanol groups, there is a marked acceleration in reconstitution times with endpoints of t=7.71 (±2.44) min (n=30) at 1% tButanol, t=7.16 (±2.65) min (n=20) at 1.5% tButanol, and t=4.74 (±1.75) min (n=20) at 2% tButanol. High and Low reconstitution endpoint values were t=1.37 min and t=11.67 min at 1% tButanol, t=3.90 min and t=15.50 min at 1.5% tButanol, and t=2.75 min and t=9.25 min at 2% tButanol. These range values would suggest that reconstitution times for albiglutide lyophilized in the presence of 2% tButanol in formulation buffer could be 3-fold faster, on the order of 10 min, than is currently recommended for albiglutide in formulation buffer, 30 min. In summary, the 2% tButanol samples are approximately 1.5 fold faster than the 1% tButanol samples, and is ~3.75-fold faster than the control sample group.

TABLE 4

Average reconstitution time endpoints for albiglutide lyophiles, grouped according to sample type.

| Grouping | Ctrl | 2% tBu | 1.5% tBu | 1% tBu | 0.5% tBu | 0.25% tBu |
|---|---|---|---|---|---|---|
| All tests - Average | 17.87 | 4.74 | 7.16 | 7.71 | 11.84 | 19.35 |
| (std dev) | 2.94 | 1.75 | 2.65 | 2.44 | 5.18 | 4.08 |
| (n) | 26 | 20 | 20 | 30 | 19 | 20 |
| Analyst 1 (syringe) - Average | 17.06 | 4.61 | 6.51 | 6.97 | 13.53 | 17.37 |
| (std dev) | 1.42 | 1.57 | 1.27 | 1.45 | 0.71 | 4.34 |
| (n) | 6 | 3 | 3 | 6 | 3 | 3 |
| Analyst 2 (syringe) - Average | 17.95 | 4.90 | 8.63 | 7.16 | 9.23 | 21.24 |
| (std dev) | 3.27 | 2.62 | 3.81 | 3.99 | 7.76 | 4.49 |
| (n) | 7 | 6 | 6 | 9 | 5 | 6 |
| Analyst 3 (syringe) - Average | 18.01 | 4.60 | 6.39 | 8.00 | 11.48 | 18.80 |
| (std dev) | 4.55 | 0.87 | 1.64 | 1.26 | 5.05 | 3.99 |
| (n) | 7 | 6 | 6 | 9 | 6 | 6 |
| Analyst 1 (pipette) - Average | 18.40 | 4.78 | 6.71 | 8.84 | 13.86 | 18.94 |
| (std dev) | 1.54 | 1.93 | 2.54 | 1.24 | 3.56 | 3.93 |
| (n) | 6 | 5 | 5 | 6 | 5 | 5 |

Figure 4:
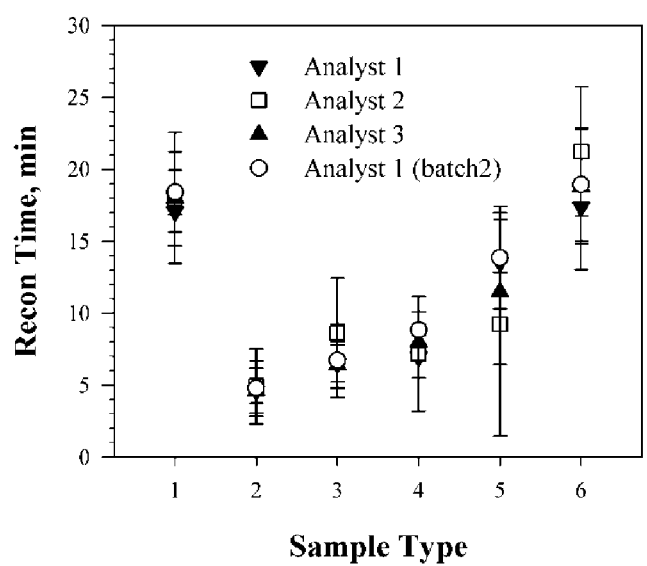
FIG. 4. Plots of lyophile reconstitution times as a function of sample number, separated by analyst and reconstitution method.

Results of lyophile recon times were also separated as a function of analyst, and comparing the method involving injection of WFI through the stopper (syringe) versus the traditional method of uncapping the vial and dispensing via Rainin pipette, summarized in Table 4 and graphically in FIG. 4. The distribution of reconstitution time endpoints within each sample group represents the dominant source of variability, with individual analyst and/or reconstitution methods having minimal influence on the average values or standard deviations for each sample type. Exceptions are for 0.5% tButanol (sample 5) and 0.25% tButanol (sample 6) which showed a wider variability of average reconstitution times and standard deviations as compared to the other samples.

Example 5—Reconstitution of Lyophilized mAbs, dAbs, and IL18

Figure 6:
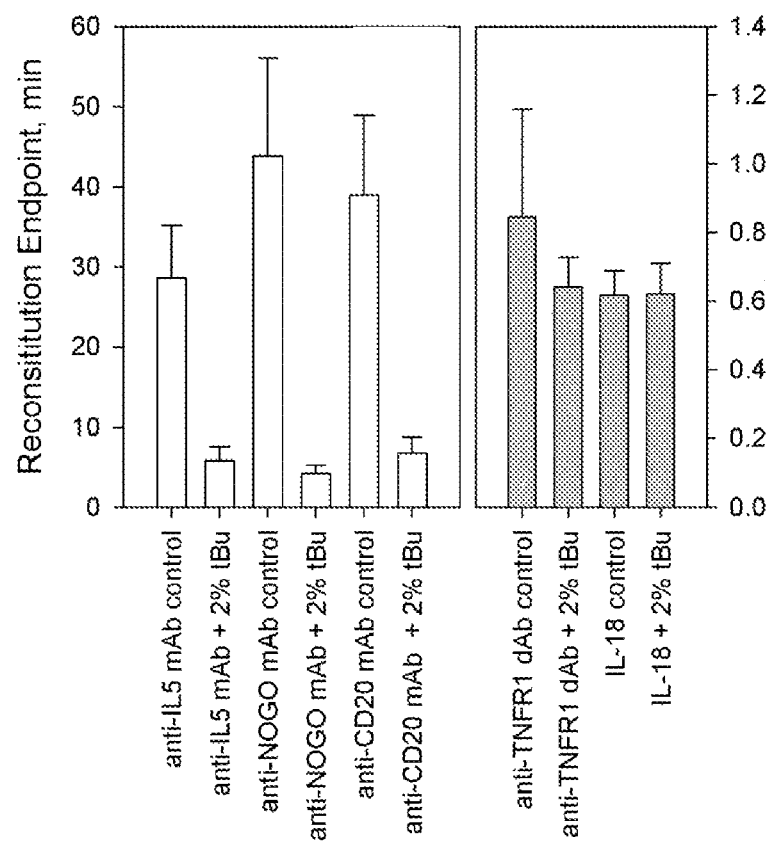
FIG. 6. Bar chart comparing reconstitution endpoints of samples, lyophilized either with or without the addition of 2% tBuOH. The bars represent the average over all tests, and whiskers one standard deviation over all tests, as a function of sample type.
Figure 7:
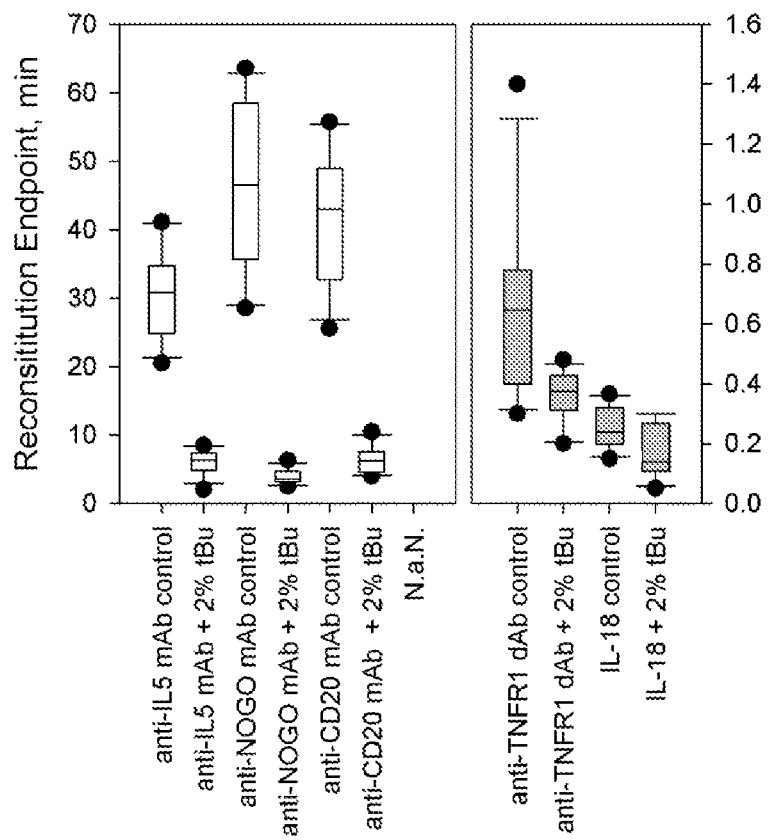
FIG. 7. Bar chart comparing reconstitution endpoints of samples, lyophilized either with or without the addition of 2% tBuOH. The bars represent the average over all tests, and whiskers one standard deviation over all tests, as a function of sample type.

Anti-NOGO mAb (SEQ ID NOS: 3 and 4), anti-TNFR1 dAb (SEQ ID NO: 5), IL18 (SEQ ID NO: 6), anti-IL5 (SEQ ID NOS: 7 and 8), and anti-CD20 (variable domains SEQ ID NOS: 9 and 10) were concentrated to the concentrations shown below in a formulation comprising 26 mM histidine, 150 mM trehalose, 0.02% polysorbate 80 (PS80), pH 6.0, in a volume of about 0.75 mL, and then lyophilized in a 2 mL vial.
79.3 mg anti-IL5 mAb
77.9 mg anti-NOGO mAb
78.2 mg anti-CD20 mAb
29.1 mg anti-TNFR1 dAb
19.0 mg IL-18
The lyophiles were reconstituted with 0.675 mL water for injection (WFI) via a 1 mL syringe and 25 G(⅝") needle through the lyophilized vial stopper (tuberculin syringes, Becton-Dickinson#309626). The volume of 0.675 mL corrects for the volume of the dry components resulting in a final volume of 0.75 mL. The reconstitution was performed using an "undisturbed method" (addition of the water was followed by immediate light mixing followed by allowing the vial to stand undisturbed). Addition of the water was performed by three different analysts (three different people performing the reconstitution step) via syringe through stopper. Individual reconstitution times are summarized in Table 5, and graphically in FIGS. 6 and 7.

Across all 5 proteins tested, those with 2% t-butanol spiked in during lyophilization had faster reconstitution times than the control groups. This is evident not only for the mAbs tested, but also can be seen for the small molecules tested; anti-TNFR1 dAb and IL-18, which also appeared to have faster reconstitution times in the presence of t-butanol.

TABLE 5

| | replicate | Anti-IL5 mAb Sample 1 | Anti-IL5 mAb w/2% Sample 2 | Anti-TNFR1 dAb Sample 3 | Anti-TNFR1 dAb w/2% Sample 4 | IL18 Sample 5 | IL18 w/2% Sample 6 | Anti-NOGO mAb Sample 7 | Anti-NOGO mAb w/2% Sample 8 | Anti-CD20 mAb Sample 9 | Anti-CD20 mAb w/2% Sample 10 |
|---|---|---|---|---|---|---|---|---|---|---|---|
| Analyst 1 | 1 | 26.73 | 2.10 | 1.40 | 0.38 | 0.20 | 0.05 | 34.45 | 6.35 | 46.30 | 7.50 |
| | 2 | 20.52 | 5.07 | 0.78 | 0.22 | 0.20 | 0.13 | 39.63 | 3.37 | 55.70 | 7.32 |
| | 3 | 24.22 | 7.08 | 0.68 | 0.43 | 0.15 | 0.10 | 28.55 | 4.78 | 54.62 | 6.35 |
| | 4 | 30.15 | 4.83 | 1.02 | 0.20 | 0.17 | 0.08 | 29.87 | 2.92 | 46.48 | 6.23 |
| Analyst 2 | 1 | 23.08 | 4.72 | 0.35 | 0.43 | 0.35 | 0.27 | 58.30 | 4.95 | 35.83 | 6.08 |
| | 2 | 34.25 | 6.87 | 0.30 | 0.42 | 0.37 | 0.27 | 53.60 | 3.93 | 32.48 | 7.67 |
| | 3 | 30.02 | 5.78 | 0.40 | 0.37 | 0.28 | 0.30 | 63.55 | 3.68 | 39.73 | 10.48 |
| | 4 | 34.92 | 8.20 | 0.40 | 0.40 | 0.33 | 0.30 | 46.77 | 3.13 | 25.58 | 8.83 |
| Analyst 3 | 1 | 40.47 | 5.97 | 0.78 | 0.30 | 0.27 | 0.18 | 58.52 | 4.48 | 49.28 | 4.43 |
| | 2 | 34.20 | 6.83 | 0.60 | 0.37 | 0.23 | 0.13 | 41.65 | 2.53 | 29.77 | 5.20 |
| | 3 | 31.52 | 8.50 | 0.62 | 0.35 | 0.23 | 0.15 | 46.35 | 3.30 | 33.32 | 4.00 |
| | 4 | 41.12 | 7.57 | 0.67 | 0.48 | 0.25 | 0.13 | 61.25 | 3.52 | 48.02 | 4.42 |
| Total samples | | 12 | 12 | 12 | 12 | 12 | 12 | 12 | 12 | 12 | 12 |
| Average | | 30.93 | 6.13 | 0.67 | 0.36 | 0.25 | 0.17 | 46.87 | 3.91 | 41.43 | 6.54 |
| STDEV | | 6.51 | 1.79 | 0.31 | 0.08 | 0.07 | 0.09 | 12.27 | 1.06 | 10.00 | 1.93 |

Note record time minutes M (Seconds/60)

Those skilled in the art will recognize, or be able to ascertain using no more than routine experimentation, many equivalents to the specific embodiments of the invention described herein. Such equivalents are intended to be encompassed by the following claims. The entire contents of all references, patents, and published patent applications cited throughout this application are hereby incorporated by reference.

We claim:

1. A method for producing a polypeptide composition with reduced reconstitution time comprising: combining a polypeptide with a volatile additive to form a liquid mixture and lyophilizing the liquid mixture to obtain a lyophilized polypeptide composition, wherein the liquid mixture comprises about 0.5% to about 2% by volume of volatile additive, and the volatile additive is t-butanol, wherein the time for reconstituting the polypeptide lyophilized in the presence of the volatile additive is reduced by more than 25% when compared to the time for reconstituting the same polypeptide lyophilized in the absence of the volatile additive.

2. The method of claim 1 wherein the polypeptide is an antigen binding polypeptide.

3. The method of claim 1 wherein the polypeptide comprises SEQ ID NO:1.

4. The method of claim 2 wherein the antigen binding polypeptide is selected from the group consisting of soluble receptor, antibody, antibody fragment, immunoglobulin single variable domain, Fab, F(ab')2, Fv, disulphide linked Fv, scFv, closed conformation multispecific antibody, disulphide-linked scFv, and diabody.

5. A method for producing a liquid polypeptide composition comprising:
    obtaining a lyophilized polypeptide produced by the method of claim 1, and reconstituting the lyophilized polypeptide with a sufficient amount of a pharmaceutically acceptable dispersing agent to yield a liquid polypeptide composition.

6. The method of claim 5 wherein the polypeptide is an antigen binding polypeptide.

7. The method of claim 5 wherein the polypeptide comprises SEQ ID NO:1.

8. The method of claim 6 wherein the antigen binding polypeptide is selected from the group consisting of soluble receptor, antibody, antibody fragment, immunoglobulin single variable domain, Fab, F(ab')2, Fv, disulphide linked Fv, scFv, closed conformation multispecific antibody, disulphide-linked scFv, and diabody.

9. A method for reducing the reconstitution time of a lyophilized polypeptide composition comprising:
    a) lyophilizing a liquid mixture comprising the polypeptide, wherein the liquid mixture comprises about 0.5% to about 2% by volume of volatile additive, wherein the volatile additive is t-butanol and
    b) reconstituting the lyophilized polypeptide with a sufficient amount of a pharmaceutically acceptable dispersing agent to the lyophilized polypeptide composition to yield a liquid polypeptide composition,
    wherein the time for reconstituting the polypeptide lyophilized in the presence of the volatile additive is reduced by more than 25% when compared to the time for reconstituting the same polypeptide lyophilized in the absence of the volatile additive.

10. The method of claim 9 wherein the polypeptide is an antigen binding polypeptide.

11. The method of claim 9 wherein the polypeptide comprises SEQ ID NO:1.

12. The method of claim 10 wherein the antigen binding polypeptide is selected from the group consisting of soluble receptor, antibody, antibody fragment, immunoglobulin single variable domain, Fab, F(ab')2, Fv, disulphide linked Fv, scFv, closed conformation multispecific antibody, disulphide-linked scFv, and diabody.

13. The method of claim 1, wherein the liquid mixture comprises about 2% by volume of volatile additive.

14. The method of claim 13, wherein the time for reconstituting the polypeptide lyophilized in the presence of the volatile additive is reduced by more than 50% compared to the time for reconstituting the same polypeptide lyophilized in the absence of the volatile additive.

15. The method of claim 9, wherein the liquid mixture comprises about 2% by volume of volatile additive.

16. The method of claim 15, wherein the time for reconstituting the polypeptide lyophilized in the presence of the volatile additive is reduced by more than 50% compared to the time for reconstituting the same polypeptide lyophilized in the absence of the volatile additive.

* * * * *

SEQUENCE LISTING

```
<160> NUMBER OF SEQ ID NOS: 10

<210> SEQ ID NO 1
<211> LENGTH: 645
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg His Gly
            20                  25                  30
```

-continued

```
Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Cys Pro Phe
                85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
            115                 120                 125

Leu Phe Gly Asp Lys Leu Cys Thr Val Ala Thr Leu Arg Glu Thr Tyr
        130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
            180                 185                 190

Thr Phe Leu Lys Lys Tyr Leu Tyr Glu Ile Ala Arg Arg His Pro Tyr
        195                 200                 205

Phe Tyr Ala Pro Glu Leu Leu Phe Phe Ala Lys Arg Tyr Lys Ala Ala
    210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

Arg Leu Lys Cys Ala Ser Leu Gln Lys Phe Gly Glu Arg Ala Phe Lys
            260                 265                 270

Ala Trp Ala Val Ala Arg Leu Ser Gln Arg Phe Pro Lys Ala Glu Phe
        275                 280                 285

Ala Glu Val Ser Lys Leu Val Thr Asp Leu Thr Lys Val His Thr Glu
    290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
                325                 330                 335

Glu Cys Cys Glu Lys Pro Leu Leu Glu Lys Ser His Cys Ile Ala Glu
            340                 345                 350

Val Glu Asn Asp Glu Met Pro Ala Asp Leu Pro Ser Leu Ala Ala Asp
        355                 360                 365

Phe Val Glu Ser Lys Asp Val Cys Lys Asn Tyr Ala Glu Ala Lys Asp
    370                 375                 380

Val Phe Leu Gly Met Phe Leu Tyr Glu Tyr Ala Arg Arg His Pro Asp
385                 390                 395                 400

Tyr Ser Val Val Leu Leu Leu Arg Leu Ala Lys Thr Tyr Glu Thr Thr
                405                 410                 415

Leu Glu Lys Cys Cys Ala Ala Ala Asp Pro His Glu Cys Tyr Ala Lys
            420                 425                 430

Val Phe Asp Glu Phe Lys Pro Leu Val Glu Glu Pro Gln Asn Leu Ile
        435                 440                 445
```

```
Lys Gln Asn Cys Glu Leu Phe Glu Gln Leu Gly Glu Tyr Lys Phe Gln
    450                 455                 460
Asn Ala Leu Leu Val Arg Tyr Thr Lys Val Pro Gln Val Ser Thr
465                 470                 475                 480
Pro Thr Leu Val Glu Val Ser Arg Asn Leu Gly Lys Val Gly Ser Lys
                485                 490                 495
Cys Cys Lys His Pro Glu Ala Lys Arg Met Pro Cys Ala Glu Asp Tyr
            500                 505                 510
Leu Ser Val Val Leu Asn Gln Leu Cys Val Leu His Glu Lys Thr Pro
        515                 520                 525
Val Ser Asp Arg Val Thr Lys Cys Cys Thr Glu Ser Leu Val Asn Arg
530                 535                 540
Arg Pro Cys Phe Ser Ala Leu Glu Val Asp Glu Thr Tyr Val Pro Lys
545                 550                 555                 560
Glu Phe Asn Ala Glu Thr Phe Thr Phe His Ala Asp Ile Cys Thr Leu
                565                 570                 575
Ser Glu Lys Glu Arg Gln Ile Lys Lys Gln Thr Ala Leu Val Glu Leu
            580                 585                 590
Val Lys His Lys Pro Lys Ala Thr Lys Glu Gln Leu Lys Ala Val Met
        595                 600                 605
Asp Asp Phe Ala Ala Phe Val Glu Lys Cys Cys Lys Ala Asp Asp Lys
610                 615                 620
Glu Thr Cys Phe Ala Glu Glu Gly Lys Lys Leu Val Ala Ala Ser Gln
625                 630                 635                 640
Ala Ala Leu Gly Leu
                645

<210> SEQ ID NO 2
<211> LENGTH: 31
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 31
<223> OTHER INFORMATION: Xaa = Gly or no amino acid

<400> SEQUENCE: 2

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg Xaa
                20                  25                  30

<210> SEQ ID NO 3
<211> LENGTH: 462
<212> TYPE: PRT
<213> ORGANISM: Artificial Sequence
<220> FEATURE:
<223> OTHER INFORMATION: Anti-NOGO mAb heavy chain.

<400> SEQUENCE: 3

Met Gly Trp Ser Cys Ile Ile Leu Phe Leu Val Ala Thr Ala Thr Gly
1               5                   10                  15
Val His Ser Gln Val Gln Leu Val Gln Ser Gly Ala Glu Val Lys Lys
                20                  25                  30
Pro Gly Ala Ser Val Lys Val Ser Cys Lys Ala Ser Gly Tyr Thr Phe
            35                  40                  45
```

```
Thr Ser Tyr Trp Met His Trp Val Arg Gln Ala Pro Gly Gln Gly Leu
     50                  55                  60
Glu Trp Ile Gly Asn Ile Asn Pro Ser Asn Gly Gly Thr Asn Tyr Asn
 65                  70                  75                  80
Glu Lys Phe Lys Ser Lys Ala Thr Met Thr Arg Asp Thr Ser Thr Ser
                 85                  90                  95
Thr Ala Tyr Met Glu Leu Ser Ser Leu Arg Ser Glu Asp Thr Ala Val
            100                 105                 110
Tyr Tyr Cys Glu Leu Met Gln Gly Tyr Trp Gly Gln Gly Thr Leu Val
            115                 120                 125
Thr Val Ser Ser Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Ala Gly Ala Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
450                 455                 460
```

```
<210> SEQ ID NO 4
<211> LENGTH: 238
<212> TYPE: PRT
<213> ORGANISM: Artificial Sequence
<220> FEATURE:
<223> OTHER INFORMATION: Anti-NOGO mAb light chain.

<400> SEQUENCE: 4

Met Gly Trp Ser Cys Ile Ile Leu Phe Leu Val Ala Thr Ala Thr Gly
 1               5                   10                  15

Val His Ser Asp Ile Val Met Thr Gln Ser Pro Leu Ser Asn Pro Val
             20                  25                  30

Thr Leu Gly Gln Pro Val Ser Ile Ser Cys Arg Ser Ser Lys Ser Leu
         35                  40                  45

Leu Tyr Lys Asp Gly Lys Thr Tyr Leu Asn Trp Phe Leu Gln Arg Pro
     50                  55                  60

Gly Gln Ser Pro Gln Leu Leu Ile Tyr Leu Met Ser Thr Arg Ala Ser
 65                  70                  75                  80

Gly Val Pro Asp Arg Phe Ser Gly Gly Ser Gly Thr Asp Phe Thr
                 85                  90                  95

Leu Lys Ile Ser Arg Val Glu Ala Glu Asp Val Gly Val Tyr Tyr Cys
             100                 105                 110

Gln Gln Leu Val Glu Tyr Pro Leu Thr Phe Gly Gln Gly Thr Lys Leu
         115                 120                 125

Glu Ile Lys Arg Thr Val Ala Ala Pro Ser Val Phe Ile Phe Pro Pro
     130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                 165                 170                 175

Ala Leu Gln Ser Gly Asn Ser Gln Glu Ser Val Thr Glu Gln Asp Ser
             180                 185                 190

Lys Asp Ser Thr Tyr Ser Leu Ser Ser Thr Leu Thr Leu Ser Lys Ala
         195                 200                 205

Asp Tyr Glu Lys His Lys Val Tyr Ala Cys Glu Val Thr His Gln Gly
     210                 215                 220

Leu Ser Ser Pro Val Thr Lys Ser Phe Asn Arg Gly Glu Cys
225                 230                 235

<210> SEQ ID NO 5
<211> LENGTH: 119
<212> TYPE: PRT
<213> ORGANISM: Artificial Sequence
<220> FEATURE:
<223> OTHER INFORMATION: Anti-TNFR1 dAb.

<400> SEQUENCE: 5

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Pro Pro Asp Gly Gln Asp Pro Phe Tyr Ala Asp Ser Val
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 6
<211> LENGTH: 157
<212> TYPE: PRT
<213> ORGANISM: Homo sapiens

<400> SEQUENCE: 6

Tyr Phe Gly Lys Leu Glu Ser Lys Leu Ser Val Ile Arg Asn Leu Asn
  1               5                  10                  15

Asp Gln Val Leu Phe Ile Asp Gln Gly Asn Arg Pro Leu Phe Glu Asp
             20                  25                  30

Met Thr Asp Ser Asp Cys Arg Asp Asn Ala Pro Arg Thr Ile Phe Ile
         35                  40                  45

Ile Ser Met Tyr Lys Asp Ser Gln Pro Arg Gly Met Ala Val Thr Ile
 50                  55                  60

Ser Val Lys Cys Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 7
<211> LENGTH: 449
<212> TYPE: PRT
<213> ORGANISM: Artificial Sequence
<220> FEATURE:
<223> OTHER INFORMATION: Anti-IL5 mAb Heavy chain.

<400> SEQUENCE: 7

Gln Val Thr Leu Arg Glu Ser Gly Pro Ala Leu Val Lys Pro Thr Gln
  1               5                  10                  15

Thr Leu Thr Leu Thr Cys Thr Val Ser Gly Phe Ser Leu Thr Ser Tyr
             20                  25                  30

Ser Val His Trp Val Arg Gln Pro Pro Gly Lys Gly Leu Glu Trp Leu
         35                  40                  45

Gly Val Ile Trp Ala Ser Gly Gly Thr Asp Tyr Asn Ser Ala Leu Met
 50                  55                  60

Ser Arg Leu Ser Ile Ser Lys Asp Thr Ser Arg Asn Gln Val Val Leu
 65                  70                  75                  80

Thr Met Thr Asn Met Asp Pro Val Asp Thr Ala Thr Tyr Tyr Cys Ala
                 85                  90                  95

Arg Asp Pro Pro Ser Ser Leu Leu Arg Leu Asp Tyr Trp Gly Arg Gly
            100                 105                 110

Thr Pro Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 8
<211> LENGTH: 220
<212> TYPE: PRT
<213> ORGANISM: Artificial Sequence
<220> FEATURE:
<223> OTHER INFORMATION: Anti-IL5 mAb light chain.

<400> SEQUENCE: 8

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30
```

```
Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 9
<211> LENGTH: 141
<212> TYPE: PRT
<213> ORGANISM: Artificial Sequence
<220> FEATURE:
<223> OTHER INFORMATION: Anti-CD20 VH

<400> SEQUENCE: 9

Met Phe Leu Gly Leu Ser Trp Ile Phe Leu Leu Ala Ile Leu Lys Gly
  1               5                  10                  15

Val Gln Cys Glu Val Gln Leu Val Glu Ser Gly Gly Gly Leu Val Pro
                20                  25                  30

Gln Gly Arg Ser Leu Arg Leu Ser Cys Ala Ala Ser Gly Phe Thr Phe
            35                  40                  45

Asn Asp Tyr Ala Met His Trp Val Arg Gln Ala Pro Gly Lys Gly Leu
 50                  55                  60

Glu Trp Val Ser Thr Ile Ser Trp Asn Ser Gly Ser Ile Gly Tyr Ala
 65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Tyr Gly Met
            115                 120                 125

Asp Val Trp Gly Gln Gly Thr Thr Val Thr Val Ser Ser
130                 135                 140

<210> SEQ ID NO 10
<211> LENGTH: 127
<212> TYPE: PRT
<213> ORGANISM: Artificial Sequence
```

```
<220> FEATURE:
<223> OTHER INFORMATION: Anti-CD20 VL

<400> SEQUENCE: 10

Met Glu Ala Pro Ala Gln Leu Leu Phe Leu Leu Leu Trp Leu Pro
 1               5                  10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys
        115                 120                 125
```